(12) United States Patent
Shoji

(10) Patent No.: US 6,855,352 B2
(45) Date of Patent: Feb. 15, 2005

(54) WILD APPLE POLYPHENOL AND PROCESS FOR PRODUCING THE SAME

(75) Inventor: Toshihiko Shoji, Nagareyama (JP)

(73) Assignee: The Nikka Whisky Distilling Co., Ltd., Tokyo (JP)

(*) Notice: Subject to any disclaimer, the term of this patent is extended or adjusted under 35 U.S.C. 154(b) by 0 days.

(21) Appl. No.: 10/363,686

(22) PCT Filed: Sep. 11, 2001

(86) PCT No.: PCT/JP01/07889

§ 371 (c)(1),
(2), (4) Date: Mar. 11, 2003

(87) PCT Pub. No.: WO02/22148

PCT Pub. Date: Mar. 21, 2002

(65) Prior Publication Data

US 2004/0014805 A1 Jan. 22, 2004

(30) Foreign Application Priority Data

Sep. 12, 2000 (JP) .................................. 2000-277228

(51) Int. Cl.$^7$ .............................................. A01N 65/00
(52) U.S. Cl. ...................................... 424/765; 424/777
(58) Field of Search ................................. 424/765, 777

(56) References Cited

U.S. PATENT DOCUMENTS

| 4,033,253 A | * | 7/1977 | Stollenwerk et al. | ....... 400/118 |
| 5,681,604 A | * | 10/1997 | Li et al. | ..................... 426/540 |
| 5,932,623 A | * | 8/1999 | Tanabe et al. | ............... 514/731 |
| 6,020,016 A | * | 2/2000 | Castleberry | .................. 426/590 |

FOREIGN PATENT DOCUMENTS

| CN | 1094251 A | * | 11/1994 |
| CN | 1095616 A | * | 11/1994 |
| CN | 1133139 A | * | 10/1996 |
| EP | 0 657 167 A1 | | 6/1995 |
| HU | 64859 T | * | 3/1994 |
| JP | 59113875 A | * | 6/1984 |
| JP | 63-214183 | | 9/1988 |
| JP | 02-006499 | | 1/1990 |
| JP | 04-178320 | | 6/1992 |
| SU | 1253580 A | * | 8/1986 |
| SU | 1745256 A | * | 7/1992 |

OTHER PUBLICATIONS

Weiner, M. Earth Medicine—Earth Food. 1980. Publisher: Fawcett Columbine, New York, NY, pp. 198–200.*
Cepeda et al. J. Texture Studies. 1999. vol. 30, No. 5, pp. 481–491.*
Cepeda et al. J. Food Engineering. 1999. vol. 41, pp. 103–107.*
Vigorov, L.I., Plant Biochemistry, Chemical Abstracts, vol. 71, No. 3, pp. 69, 10263t, July, 1969. Cited in the int'l. search rpt.
Dzhangaliev, A. D., Chemical Abstracts, vol. 80, No. 7, p. 208, 35957w, Feb. 1974, Cited in the int'l. search rpt.
Perez–Ilzarbe, et al; "Liquid Chromatographic Determination of Apple Pulp Procyanidins"; Journal of Liquid Chromatogaphry, 15(4) pp637–646 (1992) See Specification, PP 1–2.
Akamatsu, Kaneyoshi; "Japanese and Chinese Medicine—New Edition"; Ishiyaku Syuppan K.K.; pp 359–360 (1980) See Specification, PP 1–2.

* cited by examiner

Primary Examiner—Christopher R. Tate
(74) Attorney, Agent, or Firm—Armstrong, Kratz, Quintos, Hanson & Brooks, LLP

(57) ABSTRACT

A fruit polyphenol obtained by subjecting a crab apple fruit to pressing and/or extraction. The fruit polyphenol is rich in such components as condensed tannins (procyanidins), chlorogenic acid, and epicatechin. The fruit polyphenol can be produced economically and efficiently.

22 Claims, No Drawings

WILD APPLE POLYPHENOL AND PROCESS FOR PRODUCING THE SAME

TECHNICAL FIELD

The present invention relates to a fruit polyphenol derived from a crab apple fruit, out of polyphenols known to have a variety of functionalities, and a production process thereof.

BACKGROUND ART

A wide variety of polyphenols known as secondary metabolites of plants are present in the plant kingdom. Some of these polyphenols have been found to show diversified physiological activities. It has heretofore been disclosed that catechin contained in tea has physiological activities such as antibacterial activity, antioxidative activity, anticancerous activity, antiallergic activity, deodoring activity, antiviral activity and blood cholesterol oxidation inhibiting activity (See JP-A-63-214183, JP-A-2-6499, JP-A-4-178320, etc.).

Further, in JP-A-7-285876, it is reported that polyphenols contained in extracts of unripe apples, unripe pears or unripe peaches have activities such as antioxidative activity, blood pressure reducing activity, antimutagenic activity, antiallergic activity, anticariogenic activity and deodoring activity. In addition, in "Japanese and Chinese Medicine—New Edition" (author: Kaneyoshi Akamatsu, Ishiyaku Syuppan Kabushiki Kaisha, published in 1980, pp. 359 to 360, J. Liquid Chromatography, 15(4), 637 to 646(1992)), it is mentioned that apples contain tannins. However, all the mention is for apples to be eaten fresh or apples to be processed, and no mention is made of crab apples.

Thus, it has been found that tea and unripe fruits, for example, have diversified physiological activities. The present inventor has made intensive studies on a process for producing a polyphenol having a wide variety of physiological activities economically and efficiently and on raw materials. As a result, the inventor has found that crab apples contain a significantly large amount of polyphenols, particularly a condensation tannin (procyanidin). The present invention has been completed based on this finding.

DISCLOSURE OF THE INVENTION

That is, according to the present invention, a fruit polyphenol is provided which is obtained by subjecting a crab apple fruit to pressing and/or extraction.

Further, according to the present invention, a process for producing a fruit polyphenol is provided which comprises the steps of subjecting a crab apple fruit to pressing and/or extraction and then purifying the resulting juice and/or extract so as to obtain a polyphenol fraction.

In the present invention, it is preferable to add sulfurous acid in a concentration of 350 to 3,000 ppm at the time of pressing a crab apple fruit. Further, when a crab apple fruit is subjected to extraction, it is preferable to add sulfurous acid in a concentration of 100 ppm or higher if a proper amount of alcohol is mixed into the crab apple fruit which is then crushed. Then, after a clear extract is prepared, sulfurous acid is preferably added in a concentration of 50 ppm or higher so as to prevent oxidation.

BEST MODE FOR CARRYING OUT THE INVENTION

Hereinafter, the present invention will be described in detail.

A fruit polyphenol in the present invention comprises a polyphenol fraction obtained by subjecting a crab apple fruit to pressing and/or extraction and then purifying the obtained juice or extract. The purification to obtain the polyphenol fraction is carried out by treating the juice or extract with an adsorbent, and a fraction adsorbed to the adsorbent (hereinafter referred to as "adsorbed fraction") contains a polyphenol. Then, the adsorbed fraction is eluted with an anhydrous alcohol (such as ethanol) so as to obtain a purified polyphenol fraction.

This polyphenol fraction can be further concentrated to obtain a liquid preparation. Further, when the concentrated polyphenol fraction is subjected to spray-drying or freeze-drying, a powdery preparation can be obtained.

As a raw material of the polyphenol of the present invention, a crab apple fruit is used. An apple is a plant belonging to Malus of Rosaceae, and a crab apple refers to a species which has not been subjected to breeding by a human or a species which is not or cannot be eaten fresh or processed. Further, as the raw material of the polyphenol of the present invention, a ripe fruit and an unripe fruit can be used.

Illustrative examples of species of crab apples include Hu Bei Hai Tang, Yin Gui Hai Tang, Xi Fu Hai Tang, Zhong Guo Ping Guo, Cui Guo, Ya Hai Tang, Ya Sha Guo and Ya Ping Guo which are native to China, Adams Crab, Geneva, Gorgeous, Jay Darling, Eleyi, Eley Purple Crab, Malus Robusta, Makamic Crab, Profusion, Royalty, Liset Crab, Red Splendor Crab, Tar Tan, and Lemoine Purple Crab.

It is said that apples are originated in the Caucasus Province near the Caspian Sea. It is known that a vast number of crab apples have grown in areas from the Uyghur Province in China to Kazakhstan and Uzbekistan bordering the Caspian Sea since a long time ago. Particularly, in the vicinity of the Tian Shan which extends from Shin-gen and I-rei in the Uyghur Province in China to the eastern part of Kazakhstan, a large-scale old growth forest of crab apples spreads. Crab apples in this area have hardly been used by humans. The crab apple contains a large amount of preferable polyphenol component and can therefore be suitably used in the present invention.

Further, also in Europe and North America, trees of crab apples which are apples without breeding are still observed in many places. These crab trees can also be suitably used in the present invention.

As a pressing method, there can be used a method which comprises cleaning an apple fruit as a raw material, crushing and pressing the apple fruit with or without addition of sulfurous acid so as to obtain a juice, preferably adding a pectolytic enzyme, and then subjecting the resulting mixture to means such as centrifugation or filtration so as to obtain a clear juice. Meanwhile, as an extraction method, there can be used a method which comprises adding sulfurous acid to a cleaned raw material as required, mixing the material with alcohol (such as ethanol or methanol), crushing the mixture, extracting the resulting material while the material is being immersed and pressed or being refluxed under heating, concentrating the extract under a reduced pressure so as to remove the alcohol, and subjecting the concentrate to centrifugation and filtration or to distribution with an organic solvent such as hexane or chloroform and filtration so as to obtain a clear extract.

As described above, in the present invention, sulfurous acid is preferably added at the time of pressing and/or extraction. In general, when an apple is pressed to obtain a juice as described above, an appropriate antioxidant is added so as to prevent the juice from being discolored brown by oxidation. Illustrative examples of conventionally used antioxidants include sulfurous acid and vitamin C. A commonly used concentration of sulfurous acid is 200 ppm or lower. Further, to attain an antioxidative effect that is nearly the same as that of sulfurous acid, vitamin C must be added in a concentration of 1,000 ppm or higher. This is because the concentration of sulfurous acid used in production of alcoholic beverages (such as fruit wine) is lower than 350 ppm which is a maximum amount permitted to be added by the liquor tax law and it is generally not attempted to add sulfurous acid in a concentration of 350 ppm or higher. When sulfurous acid is added in a concentration of 350 ppm or higher, the obtained juice has a strong odor of sulfurous acid and cannot be drunk.

However, as a result of intensive studies made by the present inventor, it has been found that when sulfurous acid is added in a concentration of 350 to 3,000 ppm, more preferably 1,000 to 2,000 ppm, more specifically, when a sulfite such as potassium metabisulfite is added in a concentration of 350 to 3,000 ppm, more preferably 1,000 to 2,000 ppm in terms of sulfurous acid at the time of pressing an apple so as to obtain a juice, a polyphenol component which is intrinsically contained in the apple can be extracted without damaging the component. When the concentration of sulfurous acid is lower than the above range, the obtained juice undergoes an oxidation reaction, and the contents of low-molecular-weight components [such as catechin, epicatechin, procyanidin B1 (PB1), procyanidin B2 (PB2) and procyanidin C1 (PC1)] are significantly lowered although the total content of all polyphenols in the obtained juice does not change. Although details of the reaction are unknown, it is assumed that small molecule are polymerized and modified, because the total polyphenol content hardly changes.

As for vitamin C, when it is added in a concentration of 3,500 to 30,000 ppm, more preferably 10,00 to 20,000 ppm, it can produce the same effect as that obtained by addition of sulfurous acid in the above concentration range.

Meanwhile, when an extraction method is employed, sulfurous acid is preferably added in a concentration of 100 ppm or higher, when a proper amount of alcohol is mixed into above, after the alcohol is removed and centrifugation and filtration or distribution and filtration are carried out to obtain a clear extract, sulfurous acid is preferably added in a concentration of 50 ppm or higher so as to prevent oxidation.

As for a purification method, the above clear juice or clear extract is passed through a column filled with an adsorbent capable of selectively adsorbing a polyphenol and releasing the adsorbed phenol by use of an eluant, such as a styrene-divinylbenzene type synthetic adsorption resin, an anion exchange resin or an octadecyl group chemically bonded silica gel (ODS) so as to adsorb a polyphenol fraction. Then, water is passed through the column for washing. Then, a 10–100% alcohol (e.g. ethanol) solution, preferably an about 50% alcohol solution is passed through the column, whereby the polyphenol fraction can be eluted and recovered. The obtained polyphenol solution is concentrated under a reduced pressure so as to remove the alcohol, whereby a fruit polyphenol liquid preparation can be obtained. The liquid preparation may contain an organic acid such as malic acid, a fatty acid ester or the like. Further, the liquid preparation may be spray-drying or freeze-drying either as it is or after an auxiliary agent for powdering such as dextrin or the like is added, whereby a fruit polyphenol powdery preparation can be obtained.

The fruit polyphenol obtained in the present invention comprises caffeic acid derivatives, p-coumaric acid derivatives, flavan-3-ols (catechins), flavonols (quercetin glycosides), dihydrochalcones (phloretin glycosides) and the like as simple polyphenol compounds and condensed tannins (procyanidins) and the like as high-molecular polyphenol compounds. A polyphenol obtained from a crab apple contains a particularly large quantity of condensed tannins.

Further, crab apples of some type contain a specific polyphenol component in particularly large quantity, and conversely, crab apples of some other type contain almost no specific polyphenol component. By use of these crab apples, purification of the specific polyphenol component can be carried out very efficiently.

The fruit polyphenol obtained in the present invention has a variety of physiological activities. The functionalities of a polyphenol derived from an apple are disclosed in JP-A-7-285876. The polyphenol in the present invention has the activities described in the publication, i.e., antioxidative activity, blood pressure reducing activity, antimutagenic activity, antiallergic activity, anticariogenic activity and deodoring activity.

Therefore, the fruit polyphenol produced as described above can be used in drugs as agents having antioxidative activity, blood pressure reducing activity, antimutagenic activity, antiallergic activity, anticariogenic activity and deodoring activity. Drugs containing the fruit polyphenol can be prepared by a known method in the form of oral drugs such as a tablet, powders, granules, a capsule and a syrup or parenteral drugs such as a suppository, ointment, nebula and injection.

Further, the fruit polyphenol can be added to beverages and foods in general so that they can be suitably used as beverages and foods having antioxidative activity, blood pressure reducing activity, antimutagenic activity, antiallergic activity, anticariogenic activity and deodoring activity. To be more specific, the fruit polyphenol can be added to alcohol beverages, carbonated beverages, fruit beverages, lactic acid bacteria beverages, coffee, tea, ice cream, candies, chewing gums, snacks, breads, noodle, and the like.

Furthermore, the fruit polyphenol can also be added to cosmetics. Illustrative examples of cosmetics to which the fruit polyphenol can be added include skin-care cosmetics and bath cosmetics such as soap, facial wash, cream, skin milk, skin lotions, powders, perfume and lipsticks; hair-care cosmetics such as shampoo and rinse; and toothpaste.

Most of the various functionalities of the above fruit polyphenol according to the present invention are ascribable to procyanidin fractions. As described in the above description of the production process, these fractions may be oxidized and modified during production. Thus, it is important to carry out a purification step in a short time with the oxidation suppressed as much as possible. When a crab apple containing a larger amount of procyanidin that an unripe apple fruit or a crab apple having composition leaning to a specific component is used, the production step can be simplified, and separation and purification can be carried out in a shorter time.

Further, in the case of unripe fruits of cultivated species such as "Fuji", apple fruits cultivated with special care must be collected by thinning one by one carefully during their growth. Meanwhile, in the case of crab apples, they grow naturally in the field, neither a fertilizer nor a pesticide must be used for cultivation thereof, and neither efforts nor costs are required. Further, since no pesticide is used, the crab apples are high in the safety. In addition, upon harvesting of the crab apples, unlike thinning works of unripe fruits of cultivated species, all fruits on a tree can be collected. Consequently, the harvesting work is quite easy.

Hereinafter, the present invention will be further described with reference to Examples. The present invention, however, shall not be limited by these Examples in any way.

EXAMPLE 1
[General Compositional Analysis of Crab Apple Juice]

Ripe crab apples were subjected to general compositional analysis.

Samples: Various ripe crab apples shown in Table 1 and a ripe apple "Fuji" as a comparison were used.

Production Process of Samples: The fruit samples were crushed in a mixer and pressed while 1,000 ppm in terms of sulfurous acid of potassium metabisulfite was being added thereto as an antioxidant. The obtained juices were subjected to centrifugation and then filtration so as to obtain clear juices. The obtained clear juices were measured for the following items, and the results of the measurements are shown in Table 1.

(Measurement Items)

Average Weight of Individual Fruit

Acidity (in terms of malic acid)

Brix

Concentration of Saccharose: Measured by high-performance liquid chromatography

Concentration of Glucose: Measured by high-performance liquid chromatography

TABLE 1

| Kind | Average Weight of Individual Fruit (g) | Acidity (in terms of malic acid, g/L) | Brix | Concentration of Saccharose (g/L) | Concentration of Glucose (g/L) |
|---|---|---|---|---|---|
| Hu Bei Hai Tang | 6 | 19 | 15.7 | 45 | 28 |
| Yin Gyi Hai Tang | 20 | 19 | 13.7 | 31 | 14 |
| Xi Fu Hai Tang | 5 | 15 | 14.9 | 29 | 22 |
| Zhong Guo Ping Guo | 143 | 22 | 11.0 | 9.7 | 23 |
| Cui Guo | 16 | 12 | 17.0 | 22 | 45 |
| Fuji | 256 | 3.0 | 11.7 | 25 | 27 |

As shown in Table 1, the ripe crab apples were smaller than the ripe apple fruit of cultivated species. Insofar as the general analysis values thus measured, none of them particularly characterized the crab apples.

EXAMPLE 2
(Analysis of Polyphenol in Crab Apple Juice)

Various kinds of crab apple juices were prepared in the same manner as in the above Example 1. A total polyphenol content was measured by a Folin-Ciocalteu method and expressed also in terms of chlorogenic acid. Further, a total procyanidin content was measured by a Porter method and expressed also in terms of procyanidin B2. Other polyphenol components were measured quantitatively by high-performance liquid chromatography. The results are shown in Tables 2 and 3.

TABLE 2

| Kind | Total Polyphenol Content (ppm) | Chlorogenic Acid (ppm) | Epicatechin (ppm) | Total Procyanidin Content (ppm) | PB1 (ppm) | PB2 (ppm) | PC1 (ppm) |
|---|---|---|---|---|---|---|---|
| Hu Bei Hai Tang | 17442 | 104 | 517 | 13817 | 196 | 891 | 423 |
| Yin Gyi Hai Tang | 15678 | 731 | 538 | 11669 | 27 | 983 | 460 |
| Xi Fu Hai Tang | 9361 | 142 | 176 | 6420 | 45 | 272 | 125 |
| Zhong Guo Ping Guo | 3933 | 141 | 191 | 1147 | 51 | 109 | 39 |
| Cui Guo | 11583 | 629 | 345 | 7560 | 40 | 615 | 269 |
| Adams Crab | 23570 | 100 | 801 | 16827 | 81 | 1367 | 736 |
| Geneva | 6331 | 270 | 271 | 2085 | 86 | 351 | 128 |
| Gorgeous | 5671 | 64 | 21 | 1514 | trace | 80 | 14 |
| Jay Darling | 9417 | 325 | 484 | 6068 | 81 | 784 | 306 |
| Eleyi | 10466 | 566 | 558 | 9229 | 115 | 1023 | 365 |
| Eley Purple Crab | 14789 | 352 | 418 | 6374 | 45 | 845 | 379 |
| Malus Robusta | 12715 | 586 | 707 | 3901 | 203 | 669 | 326 |
| Makamic Crab | 13361 | 283 | 411 | 5379 | 169 | 731 | 294 |
| Profusion | 13792 | 208 | 442 | 7241 | 115 | 672 | 283 |
| Royalty | 26776 | 944 | 35 | 30847 | trace | 2296 | 323 |
| Liset Crab | 17334 | 22 | 511 | 21925 | 99 | 182 | 348 |
| Red Splendor Crab | 15934 | 152 | 20 | 20906 | trace | trace | 14 |
| Tar Tan | 5092 | 295 | 116 | 882 | 22 | 168 | 49 |
| L moine Purple Crab | 10156 | 136 | 342 | 3750 | 120 | 570 | 230 |
| Fuji | 2195 | 168 | 46 | 913 | 18 | 68 | 24 |

TABLE 3

| Kind | Total Polyphenol Content (ppm) | Chlorogenic Acid (ppm) | Epicatechin (ppm) | Total Procyanidin Content (ppm) | PB1 (ppm) | PB2 (ppm) | PC1 (ppm) |
| --- | --- | --- | --- | --- | --- | --- | --- |
| Da Sha Guo | 4753 | 427 | 113 | 1308 | 16 | 182 | 61 |
| Hai Tang Hua | 16017 | 193 | 557 | 10877 | 133 | 1020 | 424 |
| Lomg Dong Hai Tang | 6606 | 77 | 8 | 4798 | 2 | 13 | 5 |
| Qin Guan | 2124 | 217 | 3 | 559 | 2 | 2 | trace |
| Sha Guo | 4277 | 188 | 37 | 783 | 17 | 56 | 19 |
| Xiang Hong Sha Guo | 8159 | 498 | 189 | 4129 | 30 | 366 | 156 |
| Xiao Huang Hai Tang | 7383 | 188 | 92 | 4654 | 14 | 173 | 67 |
| Yan Tai Sha Guo | 6231 | 263 | 89 | 2963 | 20 | 152 | 48 |
| Yin Gye Hai Tang | 13243 | 569 | 321 | 7309 | 14 | 577 | 250 |
| Yarlington Mill | 7157 | 1039 | 452 | 1622 | 166 | 322 | 100 |
| Aldenham Purple Crab | 9161 | 129 | 456 | 7267 | 162 | 619 | 271 |
| Olga Crab | 5104 | 176 | 144 | 3224 | 54 | 266 | 96 |

As shown in Table 2, the crab apples have a higher total polyphenol content than Fuji which is an apple to be eaten fresh. It is obvious that the Adams Crab and Royalty species contain about 10 times as much polyphenol as Fuji. Further, in terms of the components of the polyphenol, it is obvious that most of the crab apples contain chlorogenic acid and epicatechin in large quantity. In addition, it has been disclosed that most of the crab apples contain a large quantity of condensed tannins which are responsible for many functionalities of the apple fruit polyphenol. It has also been disclosed that of the condensed tannins, the contents of dimer fraction procyanidins B1 (PB1) and B2 (PB2) and a trimer fraction procyanidin C1 (PC1) which are known to have a hair-growing effect as disclosed in JP-A-8-503021 are also very high in most of the crab apples. Further, it is also obvious that by use of Royalty containing little procyanidin B1 (PB1), a purified product of the procyanidin B2 (PB2) can be obtained easily. As for Red Splendor Crab, the total procyanidin content is high, but neither PB1 nor PB2 is detected, and the content of PC1 is also low. Therefore, it can be said that this species is an excellent material for purifying procyanidin fractions (multimers larger than a trimer) other than PB1, PB2 and PC1.

Further, as shown in Table 3, Hai Tang Hua contains at least 10 times as much procyanidins as Fuji. The species also has high contents of PB1, PB2 and PC1. Yin Gye Hai Tang contains PB2 in much larger quantity than PB1, since both PB1 and PB2 are a dimer, it is difficult to separate them, and yields thereof are low. However, by use of the species as a raw material, PB2 can be purified easily. On the other hand, Yarlington Mill is excellent as a raw material from which PB1 can be separated and purified easily. Similarly, although Lomg Dong Hai Tang has a high total procyanidin content, it has low contents of PB1, PB2 and PC1. It can be said that this species is an excellent raw material to purify procyanidin fractions (multimers larger than a trimer) other than PB1, PB2 and PC1.

EXAMPLE 3

(Analysis of Polyphenol in Juice of Crab Apple from Uyghur in China)

Apples produced in the Uyghur Province in China were collected, and polyphenol components in crab apple juices prepared by the same sample preparation process as used in the above Example 1 except that 600 ppm of sulfurous acid was added to Uyghur crab apples 1 and 2 and 350 ppm of sulfurous acid was added to an Uyghur crab apple 3 were measured. A total polyphenol content was determined by measuring absorbance at 280 nm and also expressed in terms of chlorogenic acid. Other components were quantified in the same manner as in the above Example 2. The results are shown in Table 4.

TABLE 4

| Kind | Total Polyphenol Content (ppm) | Chlorogenic Acid (ppm) | Epicatechin (ppm) | Total Procyanidin Content (ppm) | PB1 (ppm) | PB2 (ppm) | PC1 (ppm) |
| --- | --- | --- | --- | --- | --- | --- | --- |
| Uyghur Crab Apple 1 | 16418 | 1591 | 1150 | 17376 | 203 | 1161 | 558 |
| Uyghur Crab Apple 2 | 13209 | 1254 | 1130 | 16368 | 245 | 1222 | 454 |
| Uyghur Crab Apple 3 | 11770 | 1232 | 1034 | 13691 | 197 | 1107 | 407 |

The Uyghur Crab Apples 1, 2 and 3 shown in Table 4 are crab apples produced in I-rei in the Uyghur Province. These apples are ones grown in an old growth forest of crab apples, and their species are not identified. All these crab apples contain a large quantity of polyphenol. Particularly, the contents of PB1 and PB2 which are a procyanidin dimer and the content of PC1 which is a trimer are very high. While a value obtained by dividing the total content of PB1, PB2 and PC1 by the total polyphenol content is 5% for Fuji, the value is 11.7% for the crab apple 1, 14.5% for the crab apple 2, and 14.5% for the crab apple 3. Since PB1, PB2 and PC1 have a hair-growing effect, it is understood that it is preferable to use these crab apples as raw materials so as to purify a fraction containing these 3 components.

EXAMPLE 4

(Production of Polyphenol Fraction from Crab Apple Juice)

By use of a ripe crab apple produced in the Uyghur Province in China in 1999 as a raw material, a juice was prepared by the same sample preparation process as used in the above Example 1. 190 ml of the obtained juice was passed through a Sepabeads SP-850 resin column manufactured by Mitsubishi Chemical Corporation at room temperature, and the column was then washed with deionized water whose amount was three times as large as the volume of the column. After washing, a 50% ethanol aqueous solution whose amount was three times as large as the volume of the column was passed through the column so as to elute and recover a polyphenol from the resin. As a result of freeze-drying the obtained 50% ethanol fraction, 858 mg of polyphenol powder was obtained. As a result of quantifying polyphenol components in this powder by the same process as used in the above Example 2, it was found that in addition to 1.1% of catechin and 14.0% of epicatechin, 1.5% of procyanidin B1, 15.9% of procyanidin B2 and 6.8% of procyanidin C1 which are condensed tannins are contained. It was proved that a product containing a high concentration of polyphenol can be produced from an crab apple easily.

Possibility of Industrial Utilization

As described above, according to the present invention, by use of a ripe crab apple as a raw material and a specific purification process, a fruit polyphenol rich in such components as condensed tannins (procyanidins), chlorogenic acid and epicatechin can be provided economically and efficiently.

What is claimed is:

1. A fruit polyphenol fraction obtained by the process comprising the steps of:
    subjecting a crab apple fruit to a method selected from the group consisting of pressing and extraction to obtain a juice;
    adding a sulfurous acid in a concentration of 100 ppm or higher, at the time of subjecting the crab apple fruit to the method selected from the group consisting of pressing and extracting; and
    purifying the obtained juice and/or extract so as to obtain a polyphenol fraction.

2. The fruit polyphenol fraction of claim 1, wherein the crab apple is at least one selected from the group consisting of Hu Bei Hai Tang, Yin Gui Hai Tang, Xi Fu Hai Tang, Zhong Guo Ping Guo, Cui Guo, Ya Hai Tang, Ya Sha Guo, Ya Ping Guo, Adams Crab, Geneva, Gorgeous, Jay Darling, Eleyi, Eley Purple Crab, Malus Robusta, Makamic Crab, Profusion, Royalty, Liset Crab, Red Splendor Crab, Tar Tan, and Lemoine Purple Crab.

3. The fruit polyphenol fraction of claim 1, wherein the crab apple is an apple produced in the Uyghur Province in China, Kazakhstan or Uzbekistan.

4. A food or beverage containing the fruit polyphenol fraction produced by the process of claim 1.

5. A cosmetic containing the fruit polyphenol fraction produced by the process of claim 1.

6. A drug containing the fruit polyphenol produced by the process of claim 1.

7. The fruit polyphenol fraction of claim 1, wherein the polyphenol fraction comprises caffeic acid derivatives, p-coumaric acid derivatives, flavan-3-ols, flavonols, dihydrochalcones and a large quantity of condensed tannins.

8. A process for producing a fruit polyphenol fraction which comprises the steps of:
    subjecting a crab apple fruit to a method selected from the group consisting of pressing and extraction to obtain a juice;
    adding a sulfurous acid in a concentration of 100 ppm or higher, at the time of subjecting the crab apple fruit to the method selected from the group consisting of pressing and extracting; and
    purifying the obtained juice and/or extract so as to obtain a polyphenol fraction.

9. The process of claim 8, wherein the crab apple fruit is subjected to pressing and 350 to 3,000 ppm of sulfurous acid is added at the time of pressing the crab apple fruit.

10. The process of claim 8, wherein the crab apple fruit is subject to extraction which further comprises mixing the crab apple fruit with alcohol and then crushing the mixture, and wherein at least 100 ppm of sulfurous acid is added at the time of subjecting the crab apple fruit to extraction to obtain a clear extract, followed by adding at least 50 ppm of sulfurous acid after preparation of the clear extract.

11. The process of claim 8, wherein the crab apple is at least one selected from the group consisting of Hu Bei Hai Tang, Yin Gui Hai Tang, Xi Fu Hai Tang, Zhong Guo Ping Guo, Cui Guo, Ya Hai Tang, Ya Sha Guo, Ya Ping Guo, Adams Crab, Geneva, Gorgeous, Jay Darling, Eleyi, Eley Purple Crab, Malus Robusta, Makamic Crab, Profusion, Royalty, Liset Crab, Red Splendor Crab, Tar Tan, and Lemoine Purple Crab.

12. The process of claim 8, wherein the crab apple is an apple produced in the Uyghur Province in China, Kazakhstan or Uzbekistan.

13. The process of claim 8, wherein the crab apple fruit is subjected to pressing and 1,000 to 2,000 ppm of sulfurous acid is added at the time of pressing the crab apple fruit.

14. The process of claim 8, wherein the crab apple fruit is subject to pressing and 350 to 3,000 ppm of sulfite potassium metabisulfite is added at the time of pressing the crab apple fruit.

15. The process of claim 8, wherein the crab apple fruit is subject to pressing and 3,500 to 30,000 ppm of Vitamin C is added at the time of pressing the crab apple fruit.

16. The process of claim 8, wherein the crab apple fruit is subject to pressing and 10,000 to 20,000 ppm of Vitamin C is added at the time of pressing the crab apple fruit.

17. The process of claim 8, wherein the crab apple fruit is subject to pressing and a pectolytic enzyme is added at the time of pressing the crab apple fruit.

18. The process of claim 8, wherein the purification process further comprises passing the obtained juice or extract through a column filled with an adsorbent capable of selectively adsorbing a polyphenol, releasing the adsorbed phenol by an eluant then passing an alcohol solution through the column, whereby the polyphenol fraction is eluted and recovered.

19. The process of claim 18, wherein the eluant is one selected from the group consisting of styrene-divinylbenzene synthetic absorption resin, an anion exchange resin and an octadecyl group chemically bonded silica gel.

20. The process of claim 18, wherein the recovered polyphenol fraction is concentrated to obtain a liquid preparation which can be spray-dried or freeze-dried to obtain a powdery fruit polyphenol preparation.

21. The process of claim 8, wherein the crab apples are subject to extraction which further comprises mixing the crab apple fruit with alcohol and then crushing the mixture, followed by concentrating the extract under a reduced pressure to remove the alcohol.

22. The process of claim 8, wherein oxidation is suppressed during the purification step.

* * * * *